United States Patent [19]

Nakahori et al.

[11] Patent Number: 4,517,849
[45] Date of Patent: May 21, 1985

[54] SAMPLING SYSTEM FOR WATER QUALITY SENSORS

[75] Inventors: Ichiro Nakahori; Shigeki Nakayama; Mitsuo Maeda; Shiro Yamauchi; Junichiro Ozawa, all of Hyogo, Japan

[73] Assignee: Mitsubishi Denki Kabushiki Kaisha, Tokyo, Japan

[21] Appl. No.: 506,259

[22] Filed: Jun. 20, 1983

[51] Int. Cl.³ .............................................. G01N 1/16
[52] U.S. Cl. ................................................. 73/863.31
[58] Field of Search ........... 73/863.31, 863.33, 864.34, 73/864.35, 864.73

[56] References Cited

U.S. PATENT DOCUMENTS 3,468,166  9/1969  Putman ............................ 73/864.34
4,377,880  3/1983  Jackson et al. .................... 73/864.24

FOREIGN PATENT DOCUMENTS 124789  9/1979  Japan ................................ 73/863.31

OTHER PUBLICATIONS

An Antibiofouling Ozone System for Cooling Water Circuits, I Application to Fresh Water Circuits, Ozone: Science and Engineering, vol. 2, pp. 327–336, 1981, International Ozone Association, copyright 1981.

*Primary Examiner*—S. Clement Swisher
*Attorney, Agent, or Firm*—Sughrue, Mion, Zinn, Macpeak & Seas

[57] ABSTRACT

A sampling system for use in the analysis of water samples using quality sensors includes a device for intermittently supplying cleaning water containing ozone to the sensors, valves, pumps and related piping for cleaning the same.

1 Claim, 6 Drawing Figures

SAMPLING SYSTEM FOR WATER QUALITY SENSORS

BACKGROUND OF THE INVENTION

The present invention relates to a sampling system for use with water quality sensors used for monitoring the quality of water being treated in water purification or sewage treatment plants.

A sampling system for use with water quality sensors is currently used in water purification or sewage treatment plants because (1) it facilitates the maintenance and management of the sensors, (2) the construction of the sensors requires it, and (3) great economy is realized by measuring the quality of water at many points using a single sensor. An example of a conventional sampling system is shown in FIG. 1, wherein the numeral 1 indicates a sampling port, 2 is a sampling pump, 3 is a sensor, 7 is a cleaning water tank, 6 and 7 are both automatic pipe cleaner elements, 8 is a sampling pump motor control center, and 9 and 10 are each drain pits. The automatic pipe cleaner 6 consists of a pipe cleaning ball supplier 6a, cleaning control valves 6b, 6c and 6d, and a cleaning control panel 6e, whereas the cleaner 7 consists of a ball collector 7a and cleaning control valves 7b and 7c. Water sampled at port 1 with pump 2 is directed to sensor 3 through valve 7b, ball collector 7a and valve 6b, and is thereafter discharged into pit 10. In this sampling mode, cleaning valves 6c, 6d and 7b are closed. In a pipe cleaning mode, sampling pump 2 is first stopped and cleaning pump 5 is actuated. At the sample time, cleaning valves, 6c and 7b are opened, and the cleaning water in tank 4 is directed through pump 5, valve 6c, ball supplier 6a, ball collector 7a and valve 7b and is discharged into pit 9. In this cleaning mode, pipe cleaning balls are delivered from supplier 6a and as they are carried along by the cleaning water travelling to ball collector 7a, the balls clean the intermediate piping. Valve 6a controls the flow of the cleaning water and directs any returning flow to pit 10. The sequence of the above steps is controlled by control panel 6e and control center 8.

The conventional sampling system has the following defects: (1) the balls must be supplied and collected manually; (2) cleaning with the balls is possible only when the piping has smooth inner walls, and (3) the balls cannot pass through the sensor, valves and the piping around it, the sampling pump or sampling port, so these areas cannot be cleaned with the balls. For these reasons, much labor is needed in cleaning operations and frequent periodical cleaning is necessary.

SUMMARY OF THE INVENTION

Therefore, one object of the present invention is to provide a device for keeping the sampling system and water quality sensors clean over an extended period.

Another object of the invention is to provide a device that causes ozone-containing sterilizing water to flow continuously or intermittently through the sampling system not only to prevent the deposition of contaminants (e.g. algae, organic matter and sludge) on various parts of the system but also to clean off any contaminant.

DETAILED DESCRIPTION OF THE PREFERRED EMBODIMENTS

Figure 1:
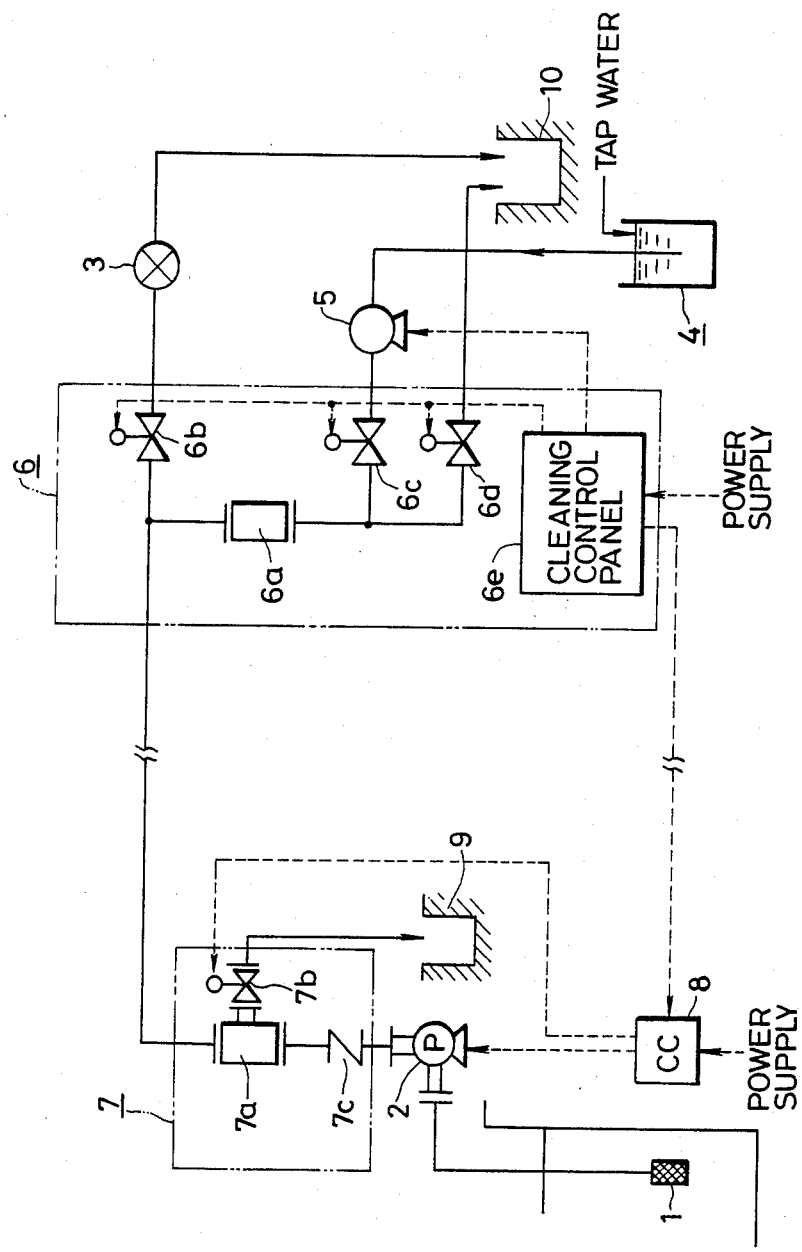
FIG. 1 is a schematic representation of the conventional sampling system.
Figure 2:
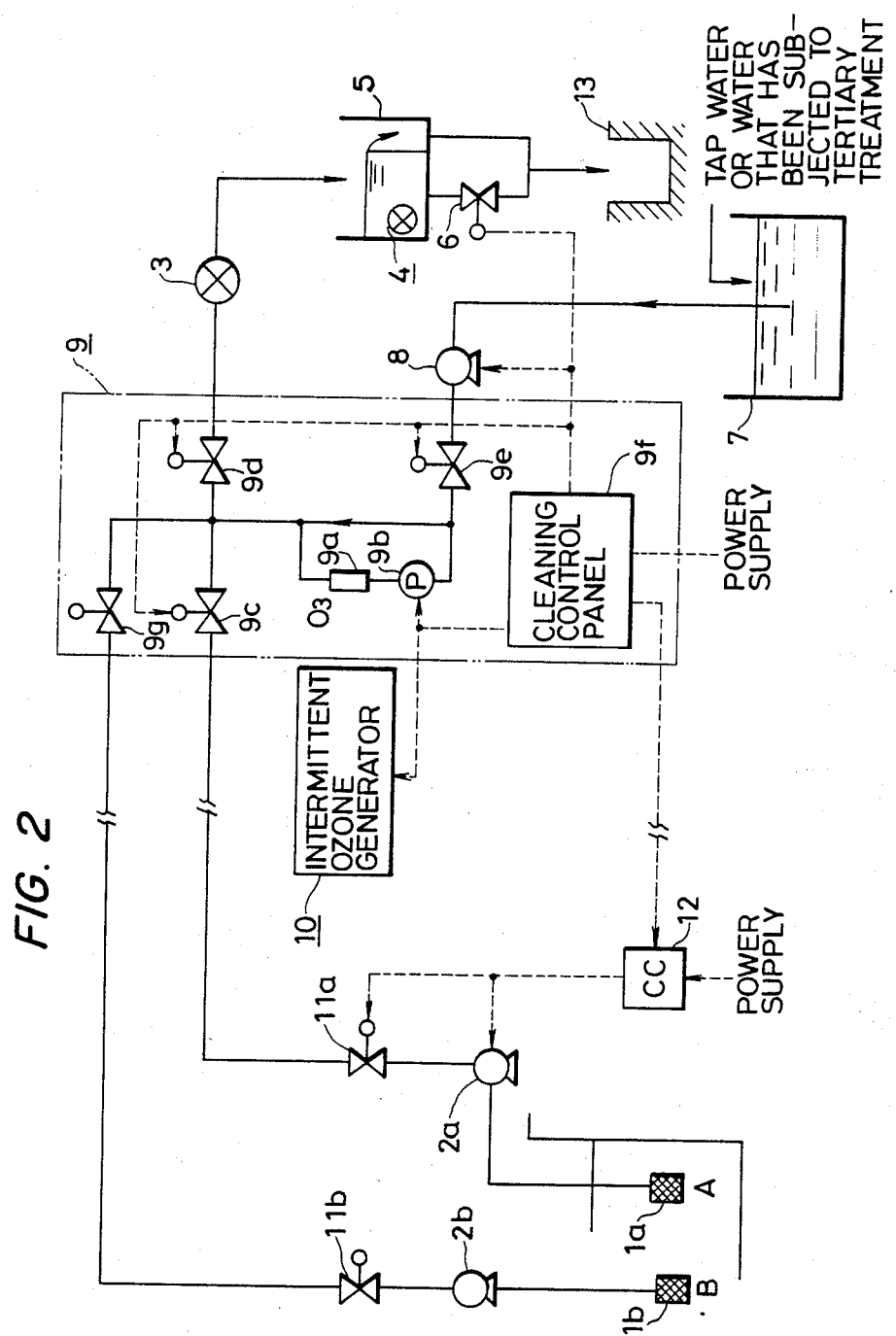
FIG. 2 shows a sampling system for a water quality sensor according to one embodiment of the present invention.

One embodiment of the sampling system according to the present invention is shown in FIG. 2, wherein the numeral 1a represents a sampling port A, 1b is a sampling port B, 2a and 2b are sampling pumps, 3 is a sensor, 4 is a submerged sensor, 5 is a water receiving tank, 6 is a drain pipe connected to the water receiving tank, 7 is a cleaning water tank, 8 is a cleaning pump, and 9 is an automatic sampling system cleaner. At 10 is shown is an intermittent ozone generator whose construction is shown in FIG. 3, 11a and 11b are cleaning water drain valves, 12 is a sampling pump motor center, and 13 is a drain pit.

The automatic sampling system cleaner 9 includes an ejector 9a for injecting ozone into water used for flushing the system, an ejector pumpr 9b, cleaning control valves 9c, 9d, 9e and 9g, and a cleaning control panel 9f.

Figure 3:
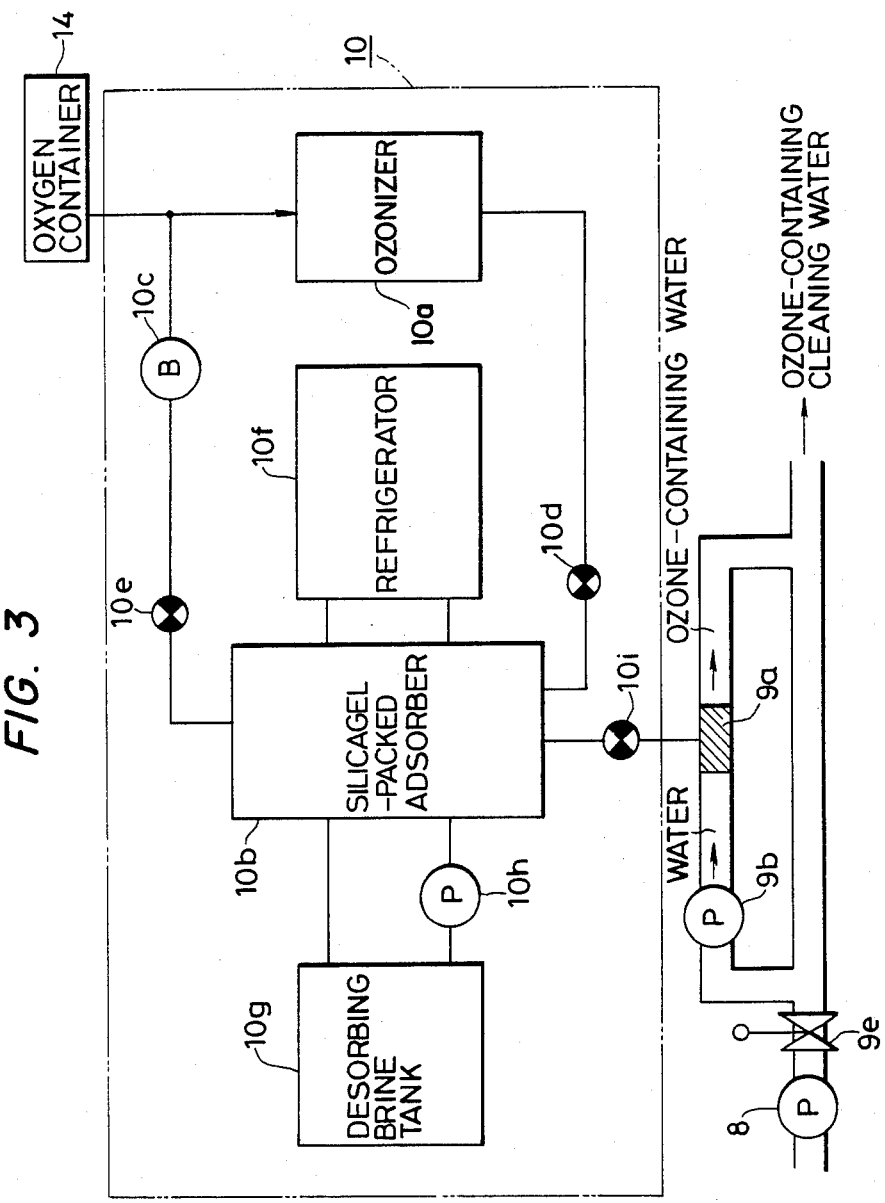
FIG. 3 shows one embodiment of the intermittent ozone generator used in the sampling system of FIG. 2.

One embodiment of the intermittent ozone generator 10 is shown in FIG. 3, wherein 10a indicates an ozonizer, 10b is a column filled with silica gel for adsorbing ozone, 10c is anoxygen circulating blower, 10e and 10d are circulation control valves, 10f is a refrigerator for the adsorbing column, 10g is a tank filled with hot brine used to desorb ozone from the silica gel, 10h is a brine supply pump, 10i is an ozone injection valve, and 14 is an oxyten container from which oxygen is supplied to ozone generator 10.

Referring to FIG. 2, water sampled at sampling port 1a using the pump 2a is directed through valves 11a, 9c and 9d to sensor 3 and sensor 4 submerged in the tank 5. The water is then discharged into drain pit 13 through an overflow mechanism in tank 5. Before sampling water at port 1b, the pump 2a is stopped, valves 11a and 9c are closed, and drain valve 6 is opened to discharge the water sampled at port 1a. Then, pump 2b is actuated and valves 11b and 9g are opened to sample water at port 1b. Sampling at port 1a alternates with the sampling at port 1b in the manner described above. Throughout the sampling mode, valve 9e remains closed.

Let us assume that sampling at point B has been completed and that pump 2b is stopped and valves 11b and 9g are closed. To start the cleaning mode, the sampling pump 2a is stopped and at the same time, valves 9c and 11a are closed. Then, the cleaning pump 8 is actuated and valve 9e is opened. At this time, drain valve 6 remains closed. Then, the intermittent ozone generator 10 and ejector pump 9b are actuated, and ozone is injected from ejector 9a into the cleaning water in tank 7. Ozone-containing cleaning water is then forced by pump 8 and sent toward sensor 3 and submerged sensor 4 through valve 9d to clean off any deposits fouling the sensors. By opening drain valve 6, the inside of tank 5 and valve 6 can also be cleaned.

Next, valves 9c and 11a are opened whereas valves 9d and 6 are closed. This causes the ozone-containing water to pass through valves 9c and 11a and be discharged into sampling port 1a through pump 2a. Then, valves 9c and 11a are closed and valves 9g and 11b are opened to supply the cleaning water through sampling port 1b through pump 2b. By this procesure, the sampling piping and pumps 2a and 2b are cleaned. After the cleaning operation, valve 9e is closed and pump 8, ejector pump 9b and the intermittent ozone generator 10 are stopped. The entire cleaning sequence is controlled by the control panel 9f and control center 12.

Referring to FIG. 3, the operation of the intermittent ozone generator 10 will now be described. Oxygen from container 14 is ozonized in ozonizer 10a by silent discharge and is forced into the adsorbing column 10b by circulation blower 10c through valve 10d. In the adsorbing column, ozone is selectively adsorbed by the silica gel. To increase the efficiency of adsorption, the adsorption column is cooled with the refrigerator 10f. Oxygen that has not been adsorbed on the silica gel is forced by the blower 10c and directed to the ozonizer through valve 10e. The ozonizer is continuously operated and the ozone produced gradually builds up in the adsorbing column. The adsorbed ozone can be desorbed by forcing hot brine from brine tank 10g into the adsorbing coumn 10b by means of pump 10h, with valves 10e and 10d being closed and the adsorbing column evacuated by ejector 9a. The desorbed ozone is ejected into water to form ozone-containing water to be again used as cleaning water.

Figure 4:
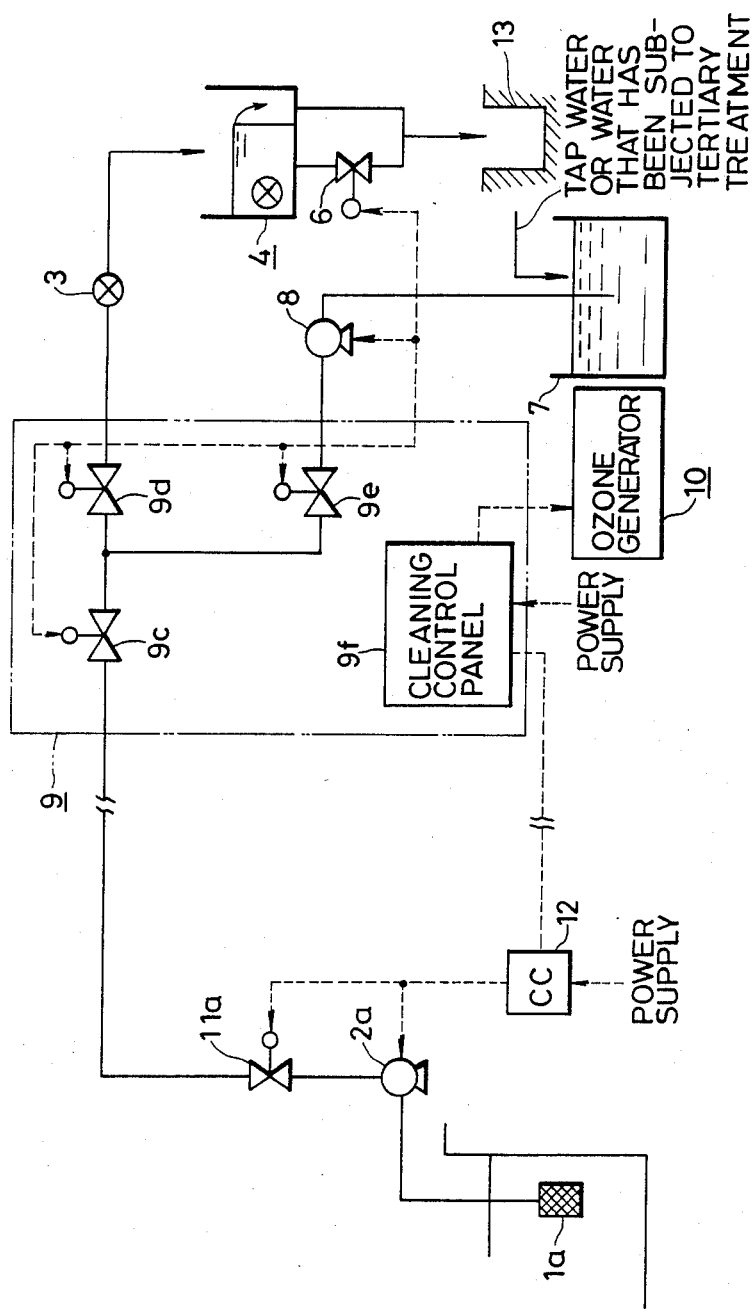
FIGS. 4, 5, 6 and show other embodiments of the sampling system of the present invention.

The intermittent ozone generator used in the embodiment of FIG. 2 may be replaced by an ordinary ozone generator to effect the present invention in a simpler form which is illustrated in FIG. 4. In the embodiment of FIG. 4, ozone produced by ozone generator 10 is directly fed to the cleaning water tank 7 where it is introduced into the water to form ozone-containing cleaning water. The operation of this ozone generator is substantially the same as that of the generator shown in FIG. 3.

Figure 5:
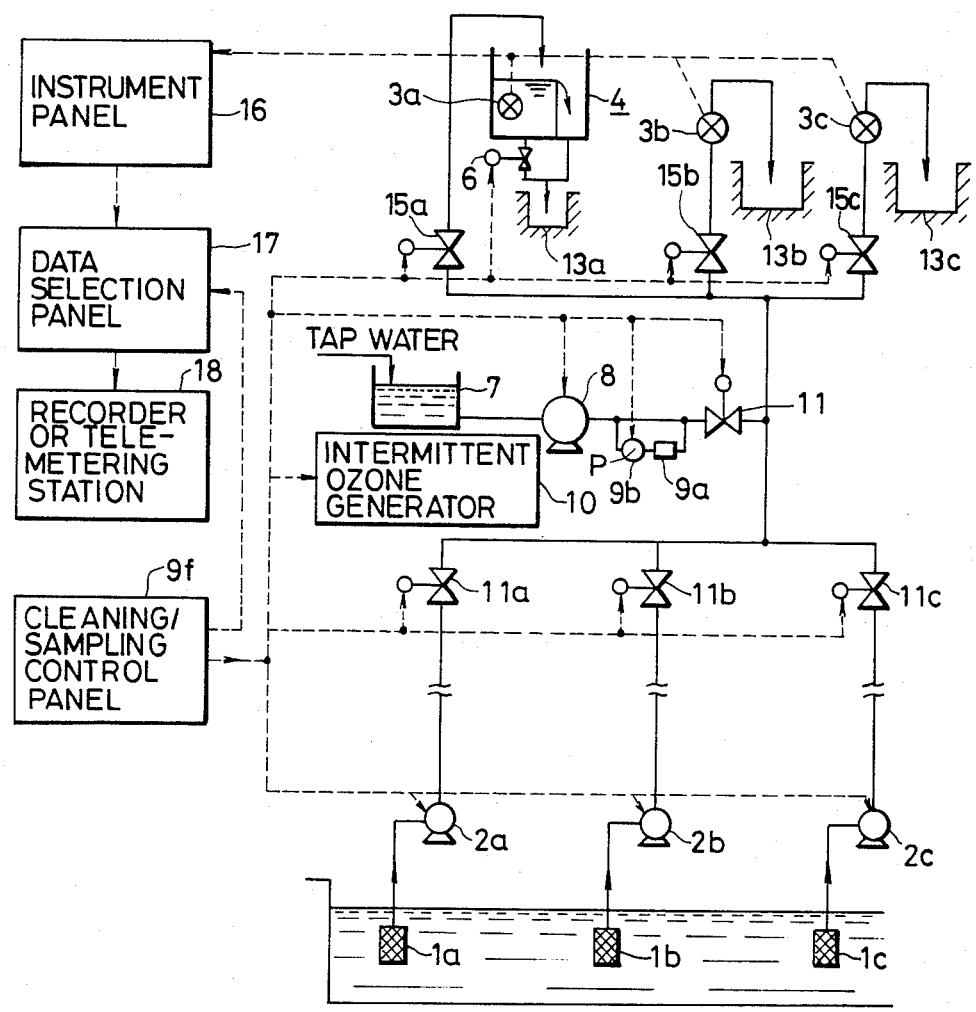

The present invention is very effective for use in the case where water is sampled at two or more points, and different types of sensors are used. The desired areas can be cleaned successively with a single cleaning system, as shown in FIG. 5. The embodiment of FIG. 5 relates to the case where sampling at many points of a single body of water is carried out, but the same principle applies to the case where sampling is performed on a plurality of such bodies.

FIG. 5 includes a cleaning sampling control panel 9f capable of controlling sampling at spots 1a, 1b and 1c, a panel of instruments 16 for analyzing the quality of the sampled water based on the data from sensors 3a, 3b and 3c, a data selection panel 17 for keying the data from the sensors with the samplihg spots, and a telemetering station 18 for recording the obtained data or sending it to a remote station. The embodiment of FIG. 5 relates to the sequential control of two or more sampling systems, and the principle of controlling one specific sampling system is the same as that described in connection with FIG. 2.

Figure 6:
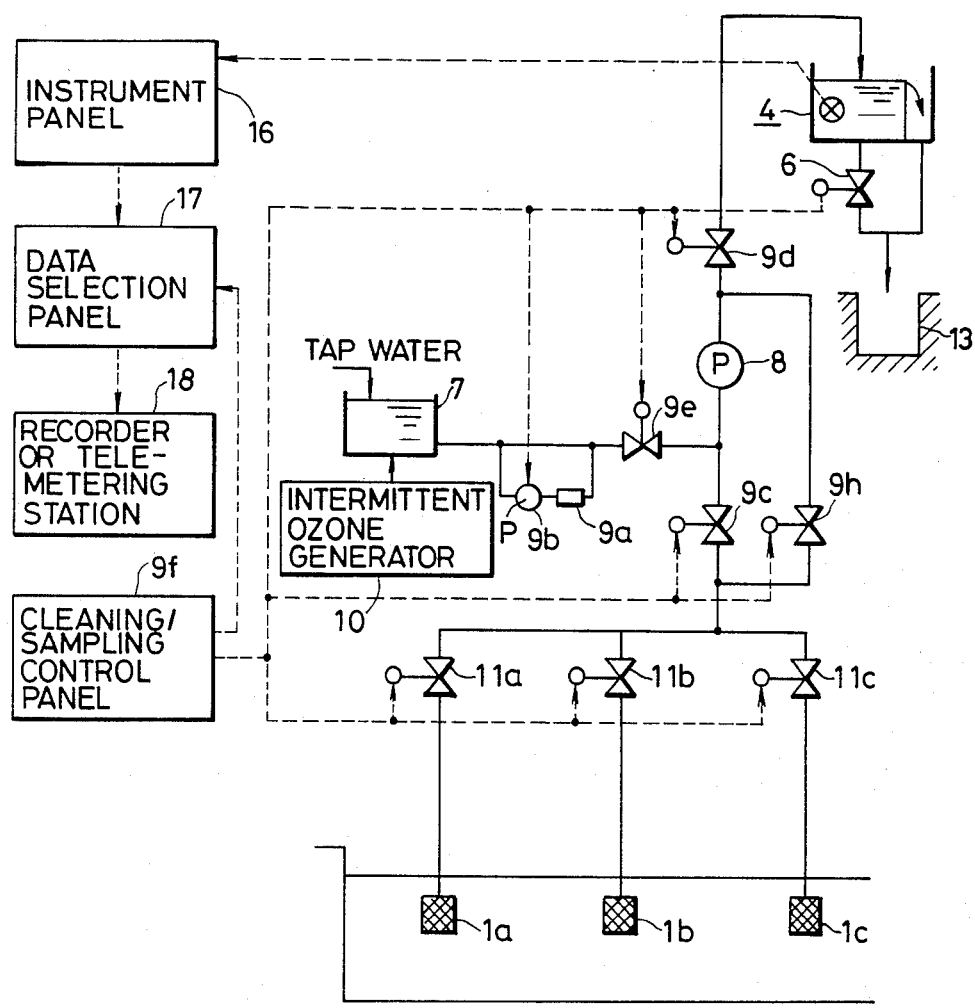

In another embodiment of the present invention, a plurality of sampling pumps can be integrated into one pump which also serves as a cleaning pump, such as simplified system being shown in FIG. 6, which includes a sampling/cleaning pump 8. In a cleaning mode, cleaning water from tank 7 is directed to sensor 4 through valves 9e and 9d, with valves 9c and 9h closed. The water cleans sensor 4, as well as water receiving tank 5 and drain valve 6 in the manner described in connection with FIG. 2. Subsequently, valve 9d is closed and valve 9h is opened to flush the cleaning water through valves 9h and 11a, or 11b or 11c to clean the sampling piping as well as these valves.

The present invention provides an effective device preventing the buildup of foul matter in a water quality sampling system which also cleans off any foul buildup automatically. The device enables very simple cleaning of the sampling system and sensors, which has conventionally involved much labor and has been considered a very dirty job. Through the cleaning of sensors and associated piping and valves, the invention contributes greatly to the maintenance and management of the sensors, and hence the precise control of various factors (e.g. chemical dosing, MLSS and DO) the water of being treated in water purification and sewage treatment plants.

What is claimed is:

1. In a sample system including means for directing water samples to at least one water quality sensor for analysis, the improvement comprising:
means for supplying ozone-containing cleaning water to areas of said system which come into contact with said water samples,
said samples being taken at more than one sampling point and being sequentially directed to a plurality of said sensors, and
said sample system further including sampling pump means proximate each said sampling point, and cleaning pump means for directing said cleaning water through said areas.

* * * * *